United States Patent
Xenopoulos

(10) Patent No.: US 9,809,799 B2
(45) Date of Patent: *Nov. 7, 2017

(54) METHODS FOR INACTIVATING VIRUSES DURING A PROTEIN PURIFICATION PROCESS

(71) Applicant: EMD Millipore Corporation, Billerica, MA (US)

(72) Inventor: Alex Xenopoulos, Billerica, MA (US)

(73) Assignee: EMD Millipore Corporation, Burlington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/390,924

(22) PCT Filed: Jun. 13, 2013

(86) PCT No.: PCT/US2013/045677
§ 371 (c)(1),
(2) Date: Oct. 6, 2014

(87) PCT Pub. No.: WO2014/004103
PCT Pub. Date: Jan. 3, 2014

(65) Prior Publication Data
US 2015/0064769 A1    Mar. 5, 2015

Related U.S. Application Data

(60) Provisional application No. 61/666,145, filed on Jun. 29, 2012.

(51) Int. Cl.
*C12N 7/00*    (2006.01)
*C07K 1/16*    (2006.01)
*C07K 1/36*    (2006.01)

(52) U.S. Cl.
CPC .............. *C12N 7/00* (2013.01); *C07K 1/36* (2013.01); *C07K 1/16* (2013.01); *C12N 2740/10061* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,877,005 | A | 3/1999 | Castor et al. |
| 6,358,534 | B1 | 3/2002 | Schwarz et al. |
| 6,468,778 | B1 | 10/2002 | Schueler et al. |
| 8,129,508 | B2 | 3/2012 | Arunakumari et al. |

(Continued)

FOREIGN PATENT DOCUMENTS

| | | |
|---|---|---|
| EP | 2290053 A1 | 3/2011 |
| JP | 61-87631 A | 5/1986 |

(Continued)

OTHER PUBLICATIONS

Roberts et al., Biologicals, 2007, 35:343-347.*

(Continued)

*Primary Examiner* — Nicole Kinsey White
(74) *Attorney, Agent, or Firm* — EMD Millipore Corporation

(57) ABSTRACT

The present application relates to novel and improved methods of achieving virus inactivation during a protein purification process.

10 Claims, 1 Drawing Sheet

(56) References Cited

U.S. PATENT DOCUMENTS

| | | | |
|---|---|---|---|
| 8,754,196 | B2 | 6/2014 | Spector et al. |
| 2002/0177693 | A1 | 11/2002 | Lebing et al. |
| 2004/0131497 | A1 | 7/2004 | Lengsfeld et al. |
| 2004/0256329 | A1 | 12/2004 | Meserol et al. |
| 2009/0105465 | A1 | 4/2009 | Arunakumari et al. |
| 2010/0135987 | A1 | 6/2010 | Hickman et al. |
| 2010/0221844 | A1 | 9/2010 | Bian et al. |
| 2013/0012689 | A1* | 1/2013 | Singh .............. B01D 15/3809 530/388.1 |
| 2013/0260419 | A1* | 10/2013 | Ransohoff .......... C12M 47/10 435/69.6 |

FOREIGN PATENT DOCUMENTS

| | | | |
|---|---|---|---|
| WO | 95/00631 | A1 | 1/1995 |
| WO | 02/092806 | A1 | 11/2002 |
| WO | 2004/058046 | A2 | 7/2004 |
| WO | 2005/090403 | A2 | 9/2005 |
| WO | 2009/045897 | A1 | 4/2009 |
| WO | 2009/138484 | A2 | 11/2009 |
| WO | 2011/028753 | A1 | 3/2011 |
| WO | 2011/037522 | A1 | 3/2011 |
| WO | 2012/014183 | A1 | 2/2012 |
| WO | 2012/051147 | A1 | 4/2012 |
| WO | WO2012/051147 | * | 4/2012 |
| WO | 2012/078677 | A2 | 6/2012 |
| WO | 2013/028330 | A2 | 2/2013 |
| WO | 2014/004281 | A1 | 1/2014 |
| WO | 2014/137903 | A2 | 9/2014 |

OTHER PUBLICATIONS

Extended European Search Report received for European Patent Application No. 13810248.8, dated Oct. 12, 2015, 7 pages.

Eibl et al., "Disposable Bioreactors in Cell Culture-Based Upstream Processing", Bio Process International, vol. 7, No. Supplement 5, Jun. 2009, pp. 18-23.

Matsushita et al., "Analysing Mass Balance of Viruses in a Coagulation-Ceramic Microfiltration Hybrid System by a Combination of the Polymerase Chain Reaction (PCR) Method and the Plaque Forming Units (PFU) Method", Water Science & Technology, vol. 53, No. 7, 2006, pp. 199-207.

Written Opinion received for PCT Patent Application No. PCT/US2013/045677, dated Sep. 17, 2013, 5 pages.

International Preliminary Report on Patentability received for PCT Patent Application No. PCT/US2013/045677, dated Jan. 8, 2015, 7 pages.

Bae et al., "Evaluation of Viral Inactivation Efficacy of a Continuous Flow Ultraviolet-C Reactor (UVivatec)", Korean Journal of Microbiology and Biotechnology, vol. 37, No. 4, 2009, pp. 377-382.

GE, "GE Healthcare: In-line Buffer Conditioning for Biopharmaceutical Manufacturing", Dec. 14, 2011, 1 page.

Li et al., "Design of a UV-C Irradiation Process for the Inactivation of Viruses in Protein Solutions", Biologicals, vol. 33, No. 2, 2005, pp. 101-110.

Perrut, Michel, "Sterilization and Virus Inactivation by Supercritical Fluids: A Review", 2012, 6 pages.

Shirasaki et al., "Feasibility of In-Line Coagulation as a Pretreatment for Ceramic Microfiltration to Remove Viruses", Journal of Water Supply: Research and Technology—AQUA, vol. 59, No. 8, 2010, pp. 501-511.

Asahikasei, "IBD Custom Solutions: Fast, Accurate Buffer Handling Tailored for your Facility", Available at <https://www.ak-bio.com/products/inline-buffer-dilution/ibd-custom-solutions/key-features/>, 2015, 15 pages.

Asahikasei, "IBD 1K System: Debottleneck Downstream Processing Facilities and Accelerate Continuous Processing with the New IBD™ 1K System", Available at <https://www.ak-bio.com/products/inline-buffer-dilution/ibd-1k-system/key-features/>, 2015, 12 pages.

Brorson et al., "Bracketed Generic Inactivation of Rodent Retroviruses by Low pH Treatment for Monoclonal Antibodies and Recombinant Proteins", Biotechnology and Bioengineering, vol. 82, No. 3, May 3, 2003, pp. 321-329.

Chothia et al., "Canonical Structures for the Hypervariable Regions of Immunoglobulins", Journal of Molecular Biology, vol. 196, No. 4, Aug. 20, 1987, pp. 901-917.

Clackson et al., "Making Antibody Fragments Using Phage Display Libraries", Nature, vol. 352, Aug. 15, 1991, pp. 624-628.

Sofer, Gail, "Virus Inactivation in the 1990s—and into the 21st Century Part 4, Culture Media, Biotechnology Products, and Vaccines", BioPharm International, Jan. 2003, pp. 50-57.

Gueffroy, Donald E., "Buffers a guide for the preparation and use of buffers in biological systems", Calbiochem Corporation, 1975, pp. 1-24.

Harrison et al., "Stability of a Single-Chain Fv Antibody Fragment When Exposed to a High Shear Environment Combined With Air-Liquid Interfaces", Biotechnology and Bioengineering, vol. 59, No. 4, Aug. 20, 1998, pp. 517-519.

Jones et al., "Replacing the Complementarity-Determining Regions in a Human Antibody with those from a Mouse", Nature, vol. 321, May 29, 1986, pp. 522-525.

K öhler et al., "Continuous Cultures of Fused Cells Secreting Antibody of Predefined Specificity", Nature, vol. 256, Aug. 7, 1975, pp. 495-497.

Mahler et al., "Protein Aggregation: Pathways, Induction Factors and Analysis", Journal of Pharmaceutical Sciences, vol. 98, No. 9, Sep. 2009, pp. 2909-2934.

Marks et al., "By-Passing Immunization : Human antibodies from V-gene Libraries Displayed on Phage", Journal of Molecular Biology, vol. 222, No. 3, Dec. 5, 1991, pp. 581-597.

Miesegaes et al., "Analysis of Viral Clearance Unit Operations for Monoclonal Antibodies", Biotechnology and Bioengineering, vol. 106, No. 2, Jun. 1, 2010, pp. 238-246.

Morrison et al., "Chimeric Human Antibody Molecules: Mouse Antigen-Binding Domains with Human Constant Region Domains", Proc. Natl. Acad. Sci. USA, vol. 81, Nov. 1984, pp. 6851-6855.

International Search Report received for PCT Patent Application No. PCT/US2013/045677, dated Sep. 17, 2013, 6 pages.

Presta, Leonard G., "Antibody Engineering", Current Opinion in Structural Biology, vol. 2, No. 4, 1992, pp. 593-596.

Riechmann et al., "Reshaping Human Antibodies for Therapy", Nature, vol. 332, Mar. 24, 1988, pp. 323-327.

Shukla et al., "Downstream Processing of Monoclonal Antibodies—Application of Platform Approaches", Journal of Chromatography B, vol. 848, 2007, pp. 28-39.

Vazquez-Rey et al., "Aggregates in Monoclonal Antibody Manufacturing Processes", Biotechnology and Bioengineering, vol. 108, No. 7, Jul. 2011, pp. 1494-1508.

Wang et al., "Antibody Structure, Instability and Formulation", Journal of Pharmaceutical Sciences, vol. 96, No. 1, Jan. 2007, pp. 1-26.

* cited by examiner

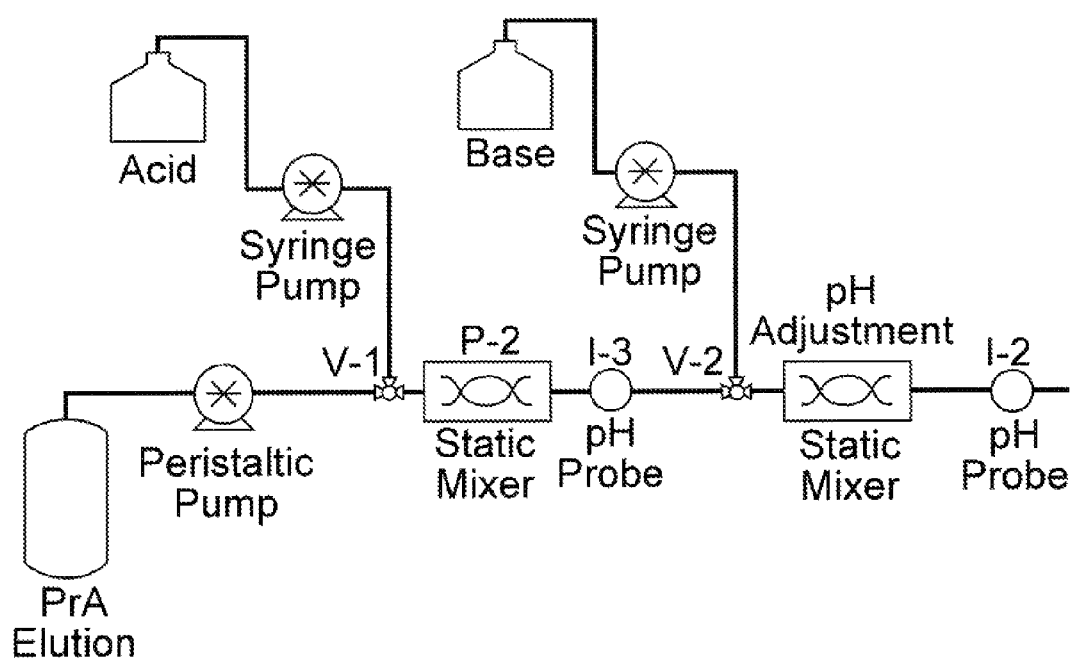

METHODS FOR INACTIVATING VIRUSES DURING A PROTEIN PURIFICATION PROCESS

RELATED APPLICATIONS

The present application claims the benefit of priority of U.S. Provisional Patent Application No. 61/666,145, filing date Jun. 29, 2012, the entire content of which is incorporated by reference herein in its entirety.

FIELD OF THE INVENTION

The present invention provides in-line methods for inactivating viruses during a protein purification process.

BACKGROUND OF THE INVENTION

Large-scale and economic purification of therapeutic proteins and especially monoclonal antibodies is an increasingly important problem for the biotechnology industry. Generally, proteins are produced by cell culture, using either mammalian or bacterial cell lines engineered to produce the protein of interest such as a monoclonal antibody. However, once produced, the proteins have to be separated from various impurities such as, host cell proteins (HCPs), endotoxins, viruses, DNA etc.

In a typical purification process, once a protein of interest is expressed in cell culture, the cell culture feed is subjected to a clarification step for removal of cell debris. The clarified cell culture feed containing the protein of interest is then subjected to one or more chromatography steps, which may include an affinity chromatography step or a cation exchange chromatography step. In order to ensure safety of a protein of interest, especially in case of a therapeutic candidate, it is necessary to inactivate any viruses which may be present in a sample containing the protein of interest during the purification process. Generally, virus inactivation is performed after a chromatography step (e.g. after affinity chromatography or after cation exchange chromatography). Typically, in a large scale process, following a chromatography step, an elution pool containing the protein of interest is collected in a large tank or reservoir and subjected to a virus inactivation step/process for an extended period of time with mixing, which may take several hours to a day or longer, in order to achieve complete inactivation of any viruses that may be present in the elution pool.

Several virus inactivation techniques are known in the art including, temperature, pH, radiation and exposure to certain chemical agents.

SUMMARY

The present invention provides methods of virus inactivation during a protein purification process, which have several advantages over the methods currently being used in the industry during protein purification. Specifically, the methods described herein obviate the need for using large tanks or reservoirs for performing the virus inactivation step during a protein purification process; reduce the overall time required for virus inactivation as well as reduce the overall physical space required to run the virus inactivation operation during a protein purification process, which in turn reduces the overall footprint for the whole purification process.

In some embodiments, a method for inactivating one or more viruses in a sample in a purification process is provided, where the method comprises continuously mixing the sample with one or more virus inactivating agents as the sample flows from the first unit operation to the second unit operation.

In some embodiments, the first unit operation comprises bind and elute chromatography and the second unit operation comprises a flow-through purification process. An exemplary bind and elute chromatography unit operation includes, but is not limited to, Protein A affinity chromatography.

In some embodiments, the flow-through purification process comprises two or more matrices selected from the group consisting of activated carbon, anion exchange chromatography media, cation exchange chromatography media and a virus filtration media.

In some embodiments, the sample comprises a Protein A eluate comprising a target molecule. Exemplary target molecules include, e.g., antibodies.

In some embodiments, the sample is mixed with one or more virus inactivating agents using one or more in-line static mixers. In other embodiments, the sample is mixed with one or more virus inactivating agents using one or more surge tanks. When static mixers are used, the flow of sample is in the laminar range.

In some embodiments, one or more virus inactivating agents are selected from the group consisting of an acid, a salt, a solvent and a detergent.

In some embodiments, a method of inactivating one or more viruses in a Protein A eluate is provided, where the method comprises mixing the eluate with one or more virus inactivating agents using an in-line static mixer, wherein complete virus inactivation is achieved in less than 10 minutes or less than 5 minutes or less than 2 minutes or less than 1 minute.

In other embodiments, a method of inactivating one or more viruses in a Protein A eluate is provided, where the method comprises mixing the eluate with one or more virus inactivating agents using a surge tank, where complete virus inactivation is achieved in less than one hour or less than 30 minutes.

In some embodiments, a method for inactivating one or more viruses comprises: (a) subjecting a sample comprising a target protein (e.g., an antibody) to a Protein A affinity chromatography process, thereby to obtain an eluate; and (b) continuously transferring the eluate to an in-line static mixer to mix one or more virus inactivating agents with the eluate for a duration of time which is equal to or less than 10 minutes, thereby to inactivate one or more viruses.

In some embodiments, the Protein A eluate which is subjected to virus inactivation methods described herein is obtained following a Protein A affinity chromatography process performed in batch mode. In other embodiments, the Protein A affinity chromatography process is performed in a continuous mode. In some embodiments, continuous mode comprises a continuous multi-column chromatography process.

In some embodiments, one or more virus inactivating agents an acid, used to perform a solution change.

In some embodiments, the eluate is continuously transferred to a flow-through purification process step following virus inactivation, in that the output from the static mixer flows directly into a flow through purification step, which may include use of two or more matrices selected from activated carbon, anion exchange media, cation exchange media and virus filtration media.

In other embodiments, the eluate is stored following virus inactivation for an extended period of time (e.g., 12 to 24 hours or overnight) in a pool or storage tank, before it is subjected to the next unit operation or process step, e.g. a flow-through purification process step or a cation exchange bind and elute chromatography step.

In some embodiments described herein, the virus inactivation methods described herein are a part of a larger protein purification process, which may include several steps including, but not limited to, e.g., culturing cells expressing protein in a bioreactor; subjecting the cell culture to clarification, which may employ one or more of precipitation, centrifugation and/or depth filtration; transferring the clarified cell culture to a bind and elute chromatography capture step (e.g., Protein A affinity chromatography); subjecting the Protein A eluate to a virus inactivation method, as described herein; subjecting the output from virus inactivation to a flow-through purification process, which employs two or more matrices selected from activated carbon, anion exchange chromatography media, cation exchange chromatography media and virus filtration media: and formulating the protein in the flow-through from the flow-through purification step using diafiltration/concentration and sterile filtration. Additional details of such processes can be found, e.g., in co-pending application having reference no. P12/107, filed concurrently herewith, and the entire contents of which are incorporated by reference herein.

In some embodiments, a fluid sample continuously flows through the entire process, as described above, from one step to the next.

BRIEF DESCRIPTION OF THE DRAWINGS

FIG. 1 is a schematic depiction of an experimental set up for virus inactivation using two in-line static mixers. The set up shown includes: (a) a peristaltic pump for sample feed, (b) two syringe pumps to deliver acid and base, c) two in-line pH probes, and (d) two static mixers. The flow rates are predetermined in batch mode based on the amount of acid/base needed to achieve the desired pH. The residence time for virus inactivation is altered by having tubes of appropriate diameter and length after each static mixer and before the pH probe.

DETAILED DESCRIPTION OF THE INVENTION

Biopharmaceutical manufacturing requires the inactivation or removal of viruses (coming from animal derived components, including mammalian cells) for drug safety and to meet the standards set forth by the Food and Drug Administration (FDA). Typical processes involve a number of viral clearance steps that cumulatively provide the necessary protection.

Some processes used in the industry involve titration of the solution containing the target protein to a low pH in order to cause destruction of any enveloped viruses and viral components. Generally, the sample containing the target protein must be retained at these conditions for an extended period of time, both because time is needed for virus inactivation but also—and more importantly—to ensure homogeneous mixing for effective virus inactivation. Therefore, in case of large scale processes, the sample containing the target protein must be incubated for an extended period of time at a low pH in order to promote efficient virus inactivation often with mixing. See, e.g., Shukla et al., J. Chromatography B., 848 (2007) 28-39, which describes virus inactivation using incubation of a protein sample for a suitable duration of time at low pH.

The pH conditions are established as a balance between a low pH value that is sufficient to cause inactivation and a high enough value to avoid denaturation of the target protein. Additionally, the sample must be exposed for a certain amount of time to cause a significant reduction, usually 2 to 6 LRV in virus activity values (See, e.g. Miesegaes et al. "Analysis of viral clearance unit operations for monoclonal antibodies." Biotechnology and Bioengineering, Vol. 106, pg 238-246 (2010)).

The three parameters that are considered important for a virus inactivation process are pH value, exposure time and temperature, assuming homogeneous mixing is present. In case of large-scale processes, mixing poses a challenge due to large volumes and additional parameters, such as mix rate and mass transfer, also become important.

In case of Fc region containing proteins (e.g. monoclonal antibodies), virus inactivation is usually performed following elution from a bind and elute chromatography process step (e.g., Protein A affinity chromatography or cation exchange chromatography) because the pH of the elution pool is closer to the desirable pH for virus inactivation. For example, in processes used in the industry today, the Protein A chromatography elution pool typically has a pH in the 3.5 to 4.0 range and the cation exchange bind and elute chromatography elution pool typically has a pH about 5.0.

In most processes used in the industry today, the elution pool containing the target protein is adjusted to the pH desired for virus inactivation and held there for a certain length of time, the combination of pH and time having been shown to result in virus inactivation. Longer times are more effective for virus inactivation, especially in case of a large-scale process, however, longer times are also known to cause protein damage. Extended exposure to low pH may result in precipitation and formation of aggregates, which is undesirable and often requires the use of a depth filter and/or a sterile filter to remove such precipitates and aggregates.

In addition to low-pH induced product quality issues, agitation in pool tanks can also cause aggregation. Proper mixing is essential in order to homogenize protein pools, and is especially important during manufacturing when protein solutions need to be treated with acid/base or buffer to adjust pH and/or conductivity (See, e.g., Vázquez-Rey et al., "Aggregates in monoclonal antibody manufacturing processes," Biotechnology and Bioengineering, Vol 108. Issue 7, pages 1494-1508 (2011)).

Several studies have shown that shear due to agitation alone may not cause protein aggregation, but may be facilitated by stirring in the presence of a gas-liquid interface (See, e.g. Mahler et al., "Protein aggregation: Pathways, induction factors and analysis." J. Pharm. Sci. 98(9):2909-2934 (2009). Harrison et al., "Stability of a single-chain Fv antibody fragment when exposed to a high shear environment combined with air-liquid interfaces," Biotechnol. Bioeng. 59:517-519 (1998)). For example, the aforementioned studies have shown that loss in activity for a single-chain Fv antibody fragment results upon stirring the protein in an incompletely filled vessel. Further, these studies showed that protein activity was not lost in the fermentation broth in the presence of antifoam in the fermentation broth. However, addition of antifoam may not be the ideal solution, especially since it would add additional purification steps and processing time to a purification process.

The present invention provides novel and improved methods for virus inactivation (also referred to as "VI" herein) during a protein purification process, which reduces the overall time for virus inactivation, the cost as well as the overall physical footprint associated with a protein purification process.

The methods described herein are able to achieve virus inactivation in a continuous manner, which significantly reduces the time associated with virus inactivation relative to most conventional processes, and in turn, reduces the time for the overall purification process.

In some embodiments described herein the methods according to the present invention employ one or more in-line static mixers for achieving virus inactivation. In other embodiments, the methods according to the present invention employs one or more surge tanks for achieving virus inactivation. The methods described herein facilitate the running of a whole purification process in a continuous manner, i.e. the sample containing the target protein can continuously flow from one process step (or unit operation) to the next process step (or unit operation), without the need to stop the flow of the sample after a process step. Accordingly, in some embodiments according to the present invention, the elution pool from an upstream bind and elute chromatography process step (e.g., Protein A affinity chromatography or cation exchange chromatography) can be subjected to virus inactivation in-line, using a static mixer and the sample flows continuously into the next process step (e.g. a flow-through purification process step). Accordingly, unlike conventional processes, the elution pool does not have to be mixed or incubated with a virus inactivating agent for an extended period of time in a pool tank or a vessel before moving on to the next process step in the purification process.

Notably, static mixers have been described for mixing a sample as it is exposed to radiation for inactivating pathogens (see, e.g. U.S. Publication No. 20040131497 and PCT Publication No. WO2002092806), or mixing a blood sample with a virus inactivation agent using a static mixer (see, e.g. PCT Publication No. WO2004058046); however, there appears to be no teaching or suggestion in the art of the use of static mixers for achieving virus inactivation during a protein purification process, as the sample flows from one unit operation to another.

The methods described herein offer several advantages over the conventional processes used in the industry today, some of which are described below.

The virus inactivation methods described herein are able to achieve more efficient mixing of the sample containing the target protein with a suitable virus inactivating agent (e.g. low pH) in less time than most conventional processes.

Due to a shorter processing time, any potential adverse effect on the target protein quality is minimized. For example, it has been shown that extended exposure to low pH conditions can result in affecting the quality of the target protein, e.g. by causing protein aggregates as well other detrimental changes (See, e.g., Wang et al. "Antibody structure, instability and formulation," J. Pharm. Sci. Vol. 96, pg. 1-26 (2007)). By having a shorter exposure time to conditions that may potentially be detrimental to product quality, any damage to the product quality can be minimized or avoided.

The present invention is based, at least in part, on a surprising and unexpected observation that even when the flow of the sample is in the laminar flow range (e.g. at slow flow-rate), efficient mixing as well as efficient virus inactivation can be achieved. Specifically, in case of the some methods described herein, because of use of in-line static mixers, the flow-rate of the sample can be controlled such that to place the flow-rate in the laminar flow range. This allows for a more predictable inactivation compared to higher flow-rates, which contributes to turbulence and leads to a narrower optimum operating window. This result is unexpected as generally, a higher flow-rate is required to achieve efficient mixing.

A process operating in the laminar flow range can be better controlled, as mixing does not depend on the presence of turbulence. For example, if the upstream flow conditions require a reduction in the flow rate, the in-line mixing process may fall out of the turbulent regime and lose some of its mixing efficiency. However, if the efficiency is dominated by the laminar flow which exists over the entire flow range, efficiency will not suffer.

The methods described herein also offer more control over the process parameters. In other words, because the methods described herein offer more control over the pH conditions, they offer more control over the entire process and enable a more robust process in general.

In addition to some of the foregoing advantages, the methods described herein also result in a smaller physical footprint of the process, e.g., by eliminating the need to use a pool tank for virus inactivation. In general, there is a growing demand for more flexible manufacturing processes that improve efficiency by reducing the overall physical footprint of the process (i.e., floor space). The methods described herein are able to reduce the overall footprint of a purification process by replacing large pool tanks that are typically used for virus inactivation with in-line static mixers or surge tanks, which are much smaller than pool tanks.

The methods described herein result in the elimination of an entire unit operation in a purification process. For example, as discussed above, generally, virus inactivation is performed in a large pool tank. In most conventional processes, the eluate from the upstream bind and elute chromatography step is collected in a pool tank, often without any mixing capabilities. Accordingly, the sample (i.e., the elution pool) has to be transferred to a proper pool tank with mixing capabilities. The pH is then adjusted to the desirable value, followed by one to two hours of incubation or longer, at the desirable pH value. Following mixing, the pH has to again be adjusted to the pH which is suitable for the next process step, which is usually a higher pH than for virus inactivation. One (sterile) or two (depth and sterile) filtration steps may also be used to remove any turbidity from the virus inactivation sample prior to subjecting the sample to the subsequent step. Often, each of these steps may be performed over the course of a day and constitute an entire separate unit operation.

In some embodiments, shorter exposure results in less or no turbidity, therefore eliminating the need for subsequent filtration steps. The methods described herein significantly simplify conventional purification processes by eliminating the entire unit operation which involves using a pool tank for virus inactivation.

The methods described herein offer easier scalability. Scaling a batch pool tank system involves increasing the stabilization time as well as the mixing efficiency which is based on the underlying mixing system (e.g., an impeller). For example, if the pool tank volume is increased by a factor of 10, then the mixing efficiency would have to be increased by a factor of 10 in order to retain the same mix time. Again, the mixing time should be minimized to safeguard the protein while maximized to achieve a certain LRV inactivation. In many cases, a mixer cannot be scaled up to an equal mixing efficiency because of limitations on the impeller size and available motor RPM. The present invention significantly increases the mixing efficiency and offers scalability based on a dimensionless number called Reynolds number (Re) which depends on the dimensions of the pipe or connecting tube which includes the in-line static mixer, the flow velocity, liquid density and viscosity. Reynolds number is defined as the ratio of density X static mixer diameter X flow rate to viscosity. Mixing efficiency can be improved by increasing the number of mixing elements of the static mixer. Better scalability and more predictive performance reduce the process parameters down to only pH and time and eliminate the dependency of success on mixing efficiency.

In-line static mixing, as described herein, allows a solution to be modified in a very short time, thereby eliminating much of the stabilization time. This allows the entire process to be compressed and results in a working volume that is reasonable for scaling and design purposes. The properties of the sample fluid can be changed by introducing a virus activation fluid into the main fluid stream through a T-valve or a manifold system. Once the fluid is in the newly desired condition, the required residence time at the inactivation pH can be guaranteed by increasing the residence time in a tube after static mixer either by increasing the length or diameter of tube or both. At the end of the required residence time, a secondary modification can be done to bring the fluid back into a condition that is desirable for the protein and the next process step.

The virus inactivation methods described herein facilitate a purification process to be run in a continuous mode, as described in more detail herein.

In order that the present invention may be more readily understood, certain terms are first defined. Additional definitions are set forth throughout the detailed description.

I. Definitions

The term "static mixer," as used herein, refers to a device for mixing two fluid materials, typically liquids (e.g., a sample containing a target protein or an eluate from a bind and elute chromatography process step). The device typically includes mixer elements (also referred to as non-moving elements) contained in cylindrical (tube) housing. The overall system design incorporates a method for delivering two streams of fluids into the static mixer. As the streams move through the mixer, the non-moving elements of the static mixer continuously blend the materials. Complete mixing depends on many variables including properties of the fluids, tube inner diameter, number of mixer elements and their design. In various embodiments described herein, a static mixer is used in-line.

The term "in-line" or "in-line operation" refers to a process of moving a liquid sample through a tube or some other conduit without storage in a vessel. Accordingly, in some embodiments according to the present invention, a static mixer is used in a "in-line operation" in a tube through which a liquid sample containing a target protein is moved from one process step to another.

The term "virus inactivation" or "VI" refers to the treatment of a sample containing one or more viruses in a manner such that the one or more viruses are no longer able to replicate or are rendered inactive. Virus inactivation may be achieved by physical means, e.g., heat, ultraviolet light, ultrasonic vibration, or using chemical means, e.g. pH change or addition of a chemical. Virus inactivation is typically a process step which is used during most protein purification processes, especially in case of purification of therapeutic proteins. In methods described herein, VI is performed using one or more in-line static mixers or surge tanks. It is understood that failure to detect one or more viruses in a sample using standard assays known in the art and those described herein, is indicative of complete inactivation of the one or more viruses following treatment of the sample with one or more virus inactivating agents.

The term "virus inactivating agent" or "virus inactivation agent." refers to any physical or chemical means capable of rendering one or more viruses inactive or unable to replicate. A virus inactivating agent, as used in the methods described herein may include a solution condition change (e.g. pH, conductivity, temperature, etc) or the addition of a solvent/detergent, a salt, a polymer, a small molecule, a drug molecule or any other suitable entity etc., which interacts with one or more viruses in a sample or a physical means (e.g., exposure to UV light, vibration etc.), such that exposure to the virus inactivating agent renders one or more viruses inactive or incapable of replicating. In a particular embodiment, a virus inactivation agent is a pH change, where the virus inactivating agent is mixed with a sample containing a target molecule (e.g., an eluate from a Protein A bind and elute chromatography step) using an in-line static mixer or a surge tank.

The term "virus removal" refers to the treatment of a virus-containing solution such that viruses are removed from the solution. Virus removal may be done through sieving (e.g. using a nanofiltration membrane with an appropriate pore size) or through adsorption (e.g. using a chromatographic device with media of a charge opposite from that of the virus).

The term "turbulent flow" refers to movement of a fluid in which subcurrents in the fluid display turbulence, moving in irregular patterns, while the overall flow is in one direction. Turbulent flow is common in non-viscous fluids moving at high velocities.

The term "laminar flow" refers to smooth, orderly movement of a fluid, in which there is no turbulence, and any given subcurrent moves more or less in parallel with any other nearby subcurrent. Laminar flow is common in viscous fluids, especially those moving at low velocities. In some embodiments according to the methods described herein, laminar flow is employed.

The term "pool tank" as used herein refers to any container, vessel, reservoir, tank or bag, which is used between process steps and has a size/volume to enable collection of the entire volume of output from a process step. Pool tanks may be used for holding or storing or manipulating solution conditions of the entire volume of output from a process step. In various embodiments according to the present invention, the methods described herein obviate the need to use one or more pool tanks.

In some embodiments, the methods described herein may use one or more surge tanks.

The term "surge tank" as used herein refers to any container or vessel or bag, which is used between process steps; where the output from a process step flows through the surge tank onto the next process step in a purification process. Accordingly, a surge tank is different from a pool tank, in that it is not intended to hold or collect the entire volume of output from a process step: but instead enables continuous flow of output from one process step to the next. In some embodiments, the volume of a surge tank used between two process steps in a methods described herein, is no more than 25% of the entire volume of the output from a process step. In another embodiment, the volume of a surge tank is no more than 10% of the entire volume of the output from a process step. In some other embodiments, the volume of a surge tank is less than 35%, or less than 30%, or less than 25%, or less than 20%, or less than 15%, or less than 10% of the entire volume of a cell culture in a bioreactor, which constitutes the starting material from which a target molecule is to be purified. In some embodiments, virus inactivation, as described herein, is achieved via a surge tank, where a surge tank is employed for mixing a suitable virus inactivation agent with a sample containing a target protein (e.g., eluate from a Protein A bind and elute chromatography step).

The term "connected process" refers to a process for purifying a target molecule, where the process comprises two or more process steps (or unit operations), which are in direct fluid communication with each other, such that fluid material continuously flows through the process step (or unit operations) in the process and is in simultaneous contact with two or more unit operations during the normal operation of the process. It is understood that at times, at least one process step (or unit operation) in the process may be temporarily isolated from the other process steps (or unit operations) by a barrier such as a valve in the closed position. This temporary isolation of individual unit operations may be necessary, for example, during start up or shut down of the process or during removal/replacement of individual unit operations.

"Protein A" and "ProA" are used interchangeably herein and encompasses Protein A recovered from a native source thereof. Protein A produced synthetically (e.g., by peptide synthesis or by recombinant techniques), and variants thereof which retain the ability to bind proteins which have a $CH_2/CH_3$ region, such as an Fc region. Protein A can be purchased commercially from Repligen. Pharmacia and Fermatech. Protein A is generally immobilized on a solid phase support material. The term "ProA" also refers to an affinity chromatography resin or column containing chromatographic solid support matrix to which is covalently attached Protein A. In a particular embodiment, Protein A used in the methods according to the present invention is an alkaline stable form of Protein A. In a particular embodiment, Protein A includes one or more Protein A domains or a functional variants or fragments thereof, as described in U.S. patent application Ser. No. 12/653,888, filed Dec. 18, 2009, and Ser. No. 13/489,999 Filed Jun. 6, 2012, both incorporated by reference herein, which relate to either wild-type multimeric forms of B, Z or C domains or multimeric variants of one or more domains of Protein A (e.g. B, Z or C domain pentamers) with each domain having a truncation of 3 or 4 amino acids from the N-terminus, where a domain may additionally include a mutation to reduce or eliminate Fab binding.

A functional derivative, fragment or variant of Protein A used in the methods according to the present invention may be characterized by a binding constant of at least $K=10^{-8}$ M, and preferably $K=10^{-9}$ M, for the Fc region of mouse IgG2a or human IgG1. An interaction obtained with such value for the binding constant is termed "high affinity binding" in the present context. Preferably, such functional derivative or variant of Protein A comprises at least part of a functional IgG binding domain of wild-type Protein A, selected from the natural domains E, D, A, B, C or engineered mutants thereof which have retained IgG binding functionality.

In various embodiments according to the present invention, the Protein A is immobilized on a solid support.

The terms "solid support," "solid phase," "matrix" and "chromatography matrix." as used interchangeably herein, generally refers to any kind of particulate sorbent, resin or other solid phase (e.g., a membrane, non-woven, monolith, etc.) which in a separation process acts as the adsorbent to separate a target molecule (e.g., an Fc region containing protein such as an immunoglobulin) from other molecules present in a mixture. Usually, the target molecule is separated from other molecules as a result of differences in rates at which the individual molecules of the mixture migrate through the matrix under the influence of a moving phase. The matrix consisting of resin particles can be put in columns or cartridges. Examples of materials for forming the matrix include polysaccharides (such as agarose and cellulose); and other mechanically stable matrices such as silica (e.g. controlled pore glass), poly(styrenedivinyl)benzene, polyacrylamide, ceramic particles and derivatives of any of the above. Typically the matrix carries one or more types of ligands. However, instances exist where the matrix alone is the chromatographic media (e.g. activated carbon, hydroxyapatite, silica, etc.)

A "ligand" is a functional group that is attached to the chromatography matrix and that determines the binding properties of the matrix. Examples of "ligands" include, but are not limited to, ion exchange groups, hydrophobic interaction groups, hydrophilic interaction groups, thiophilic interactions groups, metal affinity groups, affinity groups, bioaffinity groups, and mixed mode groups (combinations of the aforementioned). Some ligands that can be used herein include, but are not limited to, strong cation exchange groups, such as sulphopropyl, sulfonic acid; strong anion exchange groups, such as trimethylammonium chloride; weak cation exchange groups, such as carboxylic acid; weak anion exchange groups, such as $N_5N$ diethylamino or DEAE hydrophobic interaction groups, such as phenyl, butyl, propyl, hexyl: and affinity groups, such as Protein A, Protein (G, and Protein L. In various embodiments according to the invention, the ligand is Protein A or a variant or fragment thereof.

The term "chromatography," as used herein, refers to any kind of technique which separates the product of interest (e.g. a therapeutic protein or antibody) from contaminants and/or protein aggregates in a biopharmaceutical preparation.

The term "affinity chromatography" refers to a protein separation technique in which a target protein (e.g., a Fc region containing protein of interest or antibody) is specifically bound to a ligand (e.g. Protein A), which is typically immobilized onto a solid support (the ligand immobilized on the solid support is referred to herein as a "chromatography matrix"). The target protein generally retains its specific binding affinity for the ligand during the chromatographic steps, while other solutes and/or proteins in the mixture do not bind appreciably or specifically to the ligand. Binding of the target protein to the immobilized ligand allows impurities including contaminating proteins or protein impurities (e.g. HCPs) to be passed through the chromatography matrix while the target protein remains specifically bound to the immobilized ligand on the solid support material; however, some non-specific binding of the contaminating proteins onto the matrix is typically observed. The chromatography matrix is typically washed one or more times with a suitable wash buffer, in order to remove the non-specifically bound proteins (e.g., HCPs) and other impurities before eluting the bound protein from the matrix. The specifically bound protein of interest is subsequently eluted from the matrix using a suitable elution buffer which facilitates the separation of the protein of interest from the matrix. In embodiments according to the present invention, one or more intermediate wash steps are eliminated from such a process, without decreasing the purity of the eluted target protein. In other words, in some embodiments according to the present invention, a protein of interest is allowed to bind to a Protein A containing chromatography matrix and is subsequently eluted, without having the need for one or more intermediate wash steps; however, the purity of the protein of interest in the Protein A elution pool is not affected. In other embodiments, the number of intermediate wash steps are reduced compared to a process which would normally use a certain number of wash steps in order to achieve a certain level of purity of the protein of interest in the Protein A elution pool. In various embodiments according to the present invention, the level of host cell proteins is reduced in the Protein A elution pool, despite the elimination of or reduction in the number of intermediate wash steps.

The terms "ion-exchange" and "ion-exchange chromatography." as used interchangeably herein, refer to the chromatographic process in which a solute or analyte of interest in a mixture, interacts with a charged compound linked (such as by covalent attachment) to a solid phase ion exchange material, such that the solute or analyte of interest interacts non-specifically with the charged compound more or less as compared to the solute impurities or contaminants in the mixture. The contaminating solutes in the mixture elute from a column of the ion exchange material faster or slower than the solute of interest or are bound to or excluded from the resin relative to the solute of interest. "Ion-exchange chromatography" includes cation exchange, anion exchange, and mixed mode ion exchange chromatography. For example, cation exchange chromatography can bind the target molecule (e.g., a Fc region containing target protein) followed by elution (cation exchange bind and elute chromatography or "CIEX") or can predominately bind the impurities while the target molecule "flows through" the column (cation exchange flow through chromatography or "FT-CIEX"). In case of anion exchange chromatography, the solid phase material can bind the target molecule (e.g. an Fc region containing target protein) followed by elution or can predominately bind the impurities while the target molecule "flows through" the column.

The term "ion exchange matrix" refers to a chromatography matrix that is negatively charged (i.e., a cation exchange resin) or positively charged (i.e., an anion exchange resin). The charge may be provided by attaching one or more charged ligands to the matrix, e.g. by covalent linking. Alternatively, or in addition, the charge may be an inherent property of the matrix (e.g. as is the case for silica, which has an overall negative charge).

A "cation exchange matrix" refers to a chromatography matrix which is negatively charged, and which has free cations for exchange with cations in an aqueous solution contacted with the matrix. A negatively charged ligand attached to the solid phase to form the cation exchange matrix may, for example, be a carboxylate or sulfonate. Commercially available cation exchange resins include carboxy-methyl-cellulose, sulphopropyl (SP) immobilized on agarose (e.g., SP-SEPHAROSE FAST FLOW™ or SP-SEPHAROSE HIGH PERFORMANCE™, from GE Healthcare) and sulphonyl immobilized on agarose (e.g. S-SEPHAROSE FAST FLOW™ from GE Healthcare). Additional examples include FRACTOGEL® EMD $SO_3$, FRACTOGEL® EMD SE Highcap, ESHMUNO® S and FRACTOGEL® EMD COO (EMD Millipore).

A "mixed mode ion exchange matrix" or "mixed mode matrix" refers to a chromatography matrix which is covalently modified with cationic and/or anionic and hydrophobic moieties. A commercially available mixed mode ion exchange resin is BAKERBOND ABX™ (J. T. Baker, Phillipsburg, N.J.) containing weak cation exchange groups, a low concentration of anion exchange groups, and hydrophobic ligands attached to a silica gel solid phase support matrix. Mixed mode cation exchange materials typically have cation exchange and hydrophobic moieties. Suitable mixed mode cation exchange materials are CAPTO® MMC (GE Healthcare) and ESHMUNO® HCX (Merck Millipore). Mixed mode anion exchange materials typically have anion exchange and hydrophobic moieties. Suitable mixed mode anion exchange materials are CAPTO® Adhere (GE Healthcare).

The term "anion exchange matrix" is used herein to refer to a chromatography matrix which is positively charged, e.g. having one or more positively charged ligands, such as quaternary amino groups, attached thereto. Commercially available anion exchange resins include DEAE cellulose, QAE SEPHADEX™ and FAST Q SEPHAROSE™ (GE Healthcare). Additional examples include FRACTOGEL® EMD TMAE, FRACTOGEL® EMD TMAE highcap, ESHMUNO® Q and FRACTOGEL® EMD DEAE (Merck Millipore).

The terms "flow-through process," "flow-through mode." and "flow-through chromatography," as used interchangeably herein, refer to a product separation technique in which at least one product of interest contained in a biopharmaceutical preparation along with one or more impurities is intended to flow through a material, which usually binds the one or more impurities, where the product of interest usually flows-through.

The terms "bind and elute process," "bind and elute mode." and "bind and elute chromatography," as used interchangeably herein, refer to a product separation technique in which at least one product of interest contained in a biopharmaceutical preparation along with one or more impurities is contacted with a solid support under conditions which facilitate the binding of the product of interest to the solid support. The product of interest is subsequently eluted from the solid support. In some embodiments according to the methods described herein, a solid support having Protein A attached to the solid support is contacted with a sample containing a product of interest and one or more impurities under suitable conditions which facilitate the binding of the product of interest to the Protein A on the solid support, where the one or more impurities are not expected to specifically bind to the solid support. The product of interest is subsequently eluted from the Protein A containing solid support, in an attempt to separate the product of interest from the one or more impurities. In the methods described herein, subsequent to elution, the Protein A elution pool is subjected to virus inactivation using one or more static mixers or a surge tank, as described herein, where the virus inactivation can be achieved in a matter of minutes to about an hour, relative to conventional processes where virus inactivation often takes several hours.

The terms "contaminant," "impurity," and "debris," as used interchangeably herein, refer to any foreign or objectionable molecule, including a biological macromolecule such as a DNA, an RNA, one or more host cell proteins, endotoxins, lipids, aggregates and one or more additives which may be present in a sample containing the product of interest that is being separated from one or more of the foreign or objectionable molecules. Additionally, such a contaminant may include any reagent which is used in a step which may occur prior to the separation process.

The terms "Chinese hamster ovary cell protein" and "CHOP" are used interchangeably to refer to a mixture of host cell proteins ("HCP") derived from a Chinese hamster ovary ("CHO") cell culture. The HCP or CHOP is generally present as an impurity in a cell culture medium or lysate (e.g., a harvested cell culture fluid ("HCCF")) comprising a protein of interest such as an antibody or an Fc-containing protein expressed in a CHO cell). The amount of CHOP present in a mixture comprising a protein of interest provides a measure of the degree of purity for the protein of interest. HCP or CHOP includes, but is not limited to, a protein of interest expressed by the host cell, such as a CHO host cell. Typically, the amount of CHOP in a protein mixture is expressed in parts per million relative to the amount of the protein of interest in the mixture. It is understood that where the host cell is another cell type, e.g. a mammalian cell besides CHO, an *E. coli*, a yeast, an insect cell, or a plant cell, HCP refers to the proteins, other than target protein, found in a lysate of the host cell.

The term "parts per million" or "ppm" are used interchangeably herein to refer to a measure of purity of a target protein purified by a method of the invention. The units ppm refer to the amount of HCP or CHOP in nanograms/milligram per protein of interest in milligrams/milliliter (i.e., CHOP ppm=(CHOP ng/mL)/(protein of interest mg/mL), where the proteins are in solution).

The terms "clarify," "clarification," and "clarification step," as used herein, refers to a process step for removing suspended particles and or colloids, thereby to reduce turbidity, of a target molecule containing solution, as measured in NTU (nephelometric turbidity units). Clarification can be achieved by a variety of means, including centrifugation or filtration. Centrifugation could be done in a batch or continuous mode, while filtration could be done in a normal flow (e.g. depth filtration) or tangential flow mode. In processes used in the industry today, centrifugation is typically followed by depth filters intended to remove insoluble impurities, which may not have been removed by centrifugation. Furthermore, methods for enhancing clarification efficiency can be used, e.g. precipitation. Precipitation of impurities can be performed by various means such as by flocculation, pH adjustment (acid precipitation), temperature shifts, phase change due to stimulus-responsive polymers or small molecules, or any combinations of these methods. In some embodiments described herein, clarification involves any combinations of two or more of centrifugation, filtration, depth filtration and precipitation. In some embodiments, the processes and systems described herein obviate the need for centrifugation.

The terms "purifying," "separating," or "isolating," as used interchangeably herein, refer to increasing the degree of purity of a polypeptide or protein of interest or a target protein from a composition or sample comprising the protein of interest and one or more impurities. Typically, the degree of purity of the protein of interest is increased by removing (completely or partially) at least one impurity from the composition. A "purification step" may be part of an overall purification process resulting in a "homogeneous" composition or sample, which is used herein to refer to a composition or sample comprising less than 100 ppm HCP in a composition comprising the protein of interest, alternatively less than 90 ppm, less than 80 ppm, less than 70 ppm, less than 60 ppm, less than 50 ppm, less than 40 ppm, less than 30 ppm, less than 20 ppm, less than 10 ppm, less than 5 ppm, or less than 3 ppm of HCP.

In some embodiments according to the present invention, the product of interest is an immunoglobulin.

The term "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form, for example. IgM antibodies which exist in pentameric form and/or IgA antibodies which exist in monomeric, dimeric or multimeric form. The term "fragment" refers to a part or portion of an antibody or antibody chain comprising fewer amino acid residues than an intact or complete antibody or antibody chain. Fragments can be obtained via chemical or enzymatic treatment of an intact or complete antibody or antibody chain. Fragments can also be obtained by recombinant means. Exemplary fragments include Fab, Fab', F(ab')2, Fc and/or Fv fragments.

The term "antigen-binding fragment" refers to a polypeptide portion of an immunoglobulin or antibody that binds an antigen or competes with intact antibody (i.e. with the intact antibody from which they were derived) for antigen binding (i.e. specific binding). Binding fragments can be produced by recombinant DNA techniques, or by enzymatic or chemical cleavage of intact immunoglobulins. Binding fragments include Fab, Fab', F(ab')$_2$, Fv, single chains, and single-chain antibodies.

The protein of interest which is purified according to the methods described herein is one which comprises a $C_H2/C_H3$ region and therefore is amenable to purification by Protein A chromatography. The term "$C_H2/C_H3$ region" when used herein refers to those amino acid residues in the Fc region of an immunoglobulin molecule which interact with Protein A. Examples of $C_H2/C_H3$ region or Fc region-containing proteins include antibodies, immunoadhesins and fusion proteins comprising a protein of interest fused to, or conjugated with, a $C_H2/C_H3$ region or Fc region.

In a particular embodiment, methods according to the claimed invention are used for purifying a fragment of an antibody which is an Fc-region containing fragment.

The term "Fc region" and "Fc region containing protein" means that the protein contains heavy and/or light chain constant regions or domains (CH and CL regions as defined previously) of an immunoglobulin. Proteins containing an "Fc region" can possess the effector functions of an immunoglobulin constant domain. An "Fc region" such as $C_H2/C_H3$ regions, can bind selectively to affinity ligands such as Protein A or functional variants thereof. In some embodiments, an Fc region containing protein specifically binds Protein A or a functional derivative, variant or fragment thereof. In other embodiments, an Fc region containing protein specifically binds Protein G or Protein L, or functional derivatives, variants or fragments thereof.

Generally, an immunoglobulin or antibody is directed against an "antigen" of interest. Preferably, the antigen is a biologically important polypeptide and administration of the antibody to a mammal suffering from a disease or disorder can result in a therapeutic benefit in that mammal.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). "Monoclonal antibodies" may also be isolated from phage antibody libraries using the techniques described in Clackson et al., Nature 352:624-628 (1991) and Marks et al., J. Mol. Biol. 222:581-597 (1991).

Monoclonal antibodies may further include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5$^{th}$ Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody may comprise at least a portion of an immunoglobulin constant region (Fc), typically that of a human immunoglobulin. For further details, see Jones et al. Nature 321:522-525 (1986); Riechmann et al. Nature 332:323-329 (1988); and Presta, Curr. Op. Struct. Biol. 2:593-596 (1992).

A "buffer" is a solution that resists changes in pH by the action of its acid-base conjugate components. Various buffers which can be employed depending, for example, on the desired pH of the buffer are described in Buffers. A Guide for the Preparation and Use of Buffers in Biological Systems, Gueffroy, D., ed. Calbiochem Corporation (1975). Non-limiting examples of buffers include MES, MOPS, MOPSO, Tris, HEPES, phosphate, acetate, citrate, succinate, and ammonium buffers, as well as combinations of these.

The term "solution," "composition" or "sample," as used herein, refers to a mixture of a molecule of interest or target protein (e.g., an Fc region containing protein such as an antibody) and one or more impurities. In some embodiments, the sample is subjected to a clarification step and a Protein A affinity chromatography step prior to being subjected to the virus inactivation methods described herein. In some embodiments, the sample comprises cell culture feed, for example, feed from a CHO cell culture, which is subjected to clarification and a Protein A chromatography step prior to virus inactivation.

The term "non-mammalian expression systems" as used herein refers to all host cells or organisms employed to generate therapeutic proteins, where the host cells or organisms are of non-mammalian origin. Examples of non-mammalian expression systems are *E. coli* and *Pichia pastoris*.

The term "eluate" or "elution pool." as used herein, refers to a solution containing a molecule of interest obtained via elution, for example, following bind and elute chromatography (e.g., using a Protein A affinity chromatography matrix). The eluate may be subjected to one or more additional purification steps. In some embodiments according to the present invention, an elution pool is obtained, which contains a target protein, e.g. an Fc region containing protein, wherein the elution pool is subjected to virus inactivation, as described herein.

The term "conductivity" refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is milliSeimens per centimeter (mS/cm or mS), and can be measured using a commercially available conductivity meter (e.g., sold by Orion). The conductivity of a solution may be altered by changing the concentration of ions therein. For example, the concentration of a buffering agent and/or concentration of a salt (e.g. NaCl or KCl) in the solution may be altered in order to achieve the desired conductivity. In some embodiments, the salt concentration of the various buffers is modified to achieve the desired conductivity.

The "pI" or "isoelectric point" of a polypeptide refer to the pH at which the polypeptide's positive charge balances its negative charge. pI can be calculated from the net charge of the amino acid residues or sialic acid residues of attached carbohydrates of the polypeptide or can be determined by isoelectric focusing.

The term "process step" or "unit operation," as used interchangeably herein, refers to the use of one or more methods or devices to achieve a certain result in a purification process. Examples of process steps or unit operations which may be employed in a purification process include, but are not limited to, clarification, bind and elute chromatography, virus inactivation, flow-through purification and formulation. It is understood that each of the process steps or unit operations may employ more than one step or method or device to achieve the intended result of that process step or unit operation.

The term "continuous process," as used herein, refers to a process for purifying a target molecule, which includes two or more process steps (or unit operations), such that the output from one process step flows directly into the next process step in the process, without interruption, and where two or more process steps can be performed concurrently for at least a portion of their duration. In other words, in case of a continuous process, it is not necessary to complete a process step before the next process step is started, but a portion of the sample is always moving through the process steps.

In some embodiments, the different process steps are connected to be operated in a continuous manner, in some embodiments, a virus inactivation method, as described herein, constitutes a process step in a continuous purification process, where a sample flows continuously from a Protein A affinity chromatography step to the virus inactivation step to the next step in the process, which is typically a flow-through purification process step.

In some embodiments, the virus inactivation process step is performed continuously, i.e., the eluate from the previous bind and elute chromatography step (i.e. Protein A affinity chromatography) flows continuously into the virus inactivation step, which employs one or more static mixers and/or surge tanks, after which the virus inactivated eluate may be collected in a storage vessel until the next process step is performed.

II. Exemplary Virus Inactivating Agents

Viral inactivation renders viruses inactive, or unable to replicate or infect, which is important, especially in case of the target molecule being intended for therapeutic use. According, virus inactivation is typically used during a protein purification process, especially when the protein is intended for therapeutic use.

Many viruses contain lipid or protein coats that can be inactivated by chemical alteration. Rather than simply rendering the virus inactive, some viral inactivation processes are able denature the virus completely. Some of the more widely used virus inactivation processes include, e.g., use of one or more of the following: solvent/detergent inactivation (e.g. with Triton X 100); pasteurization (heating); acidic pH inactivation; and ultraviolet (UV) inactivation. It is also possible to combine two or more of these processes; e.g., perform acidic pH inactivation at elevated temperature.

Several virus inactivating agents for biotechnology products are known in the art. See, e.g., Gail Sofer, "Virus Inactivation in the 1990s—and into the 21st Century, Part 4, Culture Media. Biotechnology Products, and Vaccines," Biopharm International, January 2003, pp. 50-57), some of which are described below.

Low pH has been shown to inactivate the xenotropic murine leukemia virus (XMuLV). In one study, pH 3.5-4.0 was found to be effective at 18-26° C., and very little difference was seen in inactivation kinetics for pH 3.7 up to pH 4.1. At 2-8° C., however, pH 4.1 inactivation was slower and required up to one hour, compared to about 30 minutes for pH 3.7. Further, variability was observed for different target molecules being purified. For example, inactivation time used with one target molecule was 60 minutes, whereas for another it was 120 minutes, and further, in case of one target molecule, the virus XMuLV was not completely inactivated even after 120 minutes. Protein concentration also affected the inactivation kinetics. In buffer only, XMuLV was inactivated in 120 minutes; addition of protein prevented complete inactivation with the same pH, temperature, and exposure time. The ionic strength of the inactivating solution appeared to mitigate the effect of increasing protein concentration.

In another study, low pH was investigated for inactivation of XMuLV and pseudorabies virus (PRV) viruses in case of eight different monoclonal antibodies (MS) produced in either Sp2/0 or NS0 mouse cell lines. The pH values used ranged between 3.14 and 3.62, resulting in LRVs ranging from around 5 to above 6 (i.e. virus cannot be measured in the sample). These data are being used to support generic virus inactivation approaches. A different study of 13 products, mostly but not all MAbs, illustrated the ability of pH 3.6-4.0 to inactivate several different viruses in five to 60 minutes.

Caprylate has been found to inactivate lipid-enveloped viruses in MAb production processes. Cell culture harvest broth containing a *Pseudomonas* exotoxin A-monoclonal antibody conjugate and a *Pseudomonas* monoclonal IgM were each spiked with viruses. Herpes simplex virus-1 (HSV-1) and Vesicular stomatitis virus (VSV) viruses were completely inactivated at 20° C., in less than 60 minutes. However, at 5° C., only partial inactivation of VSV was shown after 120 minutes. A non-ionized form of the caprylate is maintained over a broad pH range, and the non-ionized form is effective in viral inactivation at concentrations between 0.001 and 0.07 weight %. VSV and vaccinia virus were inactivated slower than HSV-1 at pH 6.3.

Detergents have also been used as a virus inactivation agent. Triton X-100 (0.5%, 4° C.) completely inactivated respiratory syncytial virus (RSV) and Friend murine leukemia virus (FrMuLV) viruses within four hours without influencing the binding capacity of a number of MAbs. Log 10 reduction values were >3.8 for FrMuLV and >5.4 for RSV. Other data have shown that MuLV was not inactivated by 0.1 to 1% Tween.

Solvents/detergents (S/D) are commonly used for virus inactivation with plasma proteins. S/D is also used for inactivation of enveloped viruses during production of recombinant proteins and MAbs. For example, during the production of B-domain deleted recombinant factor VIII, S/D is used for virus inactivation. Although no viruses may be associated with the CHO cell line used for production, S/D can be added after a cation exchange step. Concentrations of 0.3% TNBP and 1% Triton X-100 are targeted for at least 30 minutes. S/D treatment has been shown to completely and rapidly inactivated all the enveloped viruses tested, which include *parainfluenza*-3 virus (P1-3), XMuLV, infectious bovine rhinotracheitis virus (IBR), and malignant catarrhal fever virus (MCF). (See, Sofer et al. Id.)

Beta-propiolactone has been proposed for viral inactivation in naked DNA vaccines. It was found that for a 16-hour treatment at 4° C., the initial concentration of β-propiolactone should not exceed 0.25% in order to prevent loss of gene expression.

In some embodiments according to the present invention, virus inactivation employs exposure of the sample containing the target protein to acidic or low pH. Accordingly, in some embodiments described herein, virus inactivation employs exposure of the output or eluate from the bind and elute chromatography step, which is upstream of virus inactivation, to acidic pH in-line using a static mixer. The pH used for virus inactivation is typically less than 5.0, or between 3.0 and 4.0. In some embodiments, the pH is 3.6 or lower. The duration of time used for virus inactivation, when an in-line static mixer tank is used, is 10 minutes or less, or 5 minutes or less, or 2 minutes or less, or 1 minute or less. In other embodiments, a surge tank is used between the bind and elute chromatography step and the flow-through process step. The duration of time for virus inactivation, when a surge tank is used, is typically 1 hour or less, or 30 minutes or less. In case of both use of in-line static mixers or surge tanks, the virus inactivation enables the process to be run continuously, rather than having to collect the sample in a pool tank for virus inactivation.

III. Exemplary Viruses and Determining Virus Inactivation

Virus may be "cleared" by two main mechanisms: removal (e.g. by filtration or chromatography) or inactivation (e.g. low pH, detergent, or irradiation). Regulatory recommendations for biopharmaceutical viral clearance can be found in several documents issued by the FDA and EMEA.

The viral clearance capabilities of a process are assessed using scaled-down versions of individual unit operations. A sample of representative process feed is "spiked" with a known quantity of virus to simulate a viral contamination, and the amount of virus removed or inactivated by the operation is measured. It is recommended that the amount of virus used for the spike should be "as high as possible to determine the capacity of the production step to inactivate/remove viruses adequately." However, the virus spike volume must not be so great that the composition of the production material is significantly altered a 10% spike volume is generally regarded as the maximum acceptable spike.

Virus is generally measured from samples collected before and after individual unit operations in a purification process using assays that quantify infectious virus particles. Clearance is reported in terms of the $Log_{10}$ reduction achieved (log reduction value or LRV). When a unit operation achieves clearance to such a degree that no virus is detected in the processed material, the minimal LRV is determined using a calculation dependent upon the virus titer in the starting feed and the amount of final material sampled. Consequently, the LRV that can be claimed for highly effective clearance steps can be raised by using high titer virus stocks that allow high levels of spike challenge, and large-volume virus assays that increase assay sensitivity. Conversely, demonstrable LRV can be lowered when feed materials are cytotoxic or interfere with viral infection of the detection cells, as this may require sample dilution, which decreases assay sensitivity.

Several methods are known in the art to assay for virus infectivity. The Tissue Culture Infectious Dose 50% assay is one such method for counting the number of infectious viral particles in a sample. The $TCID_{50}$ is the quantity of a pathogenic agent (virus) that will produce a cytopathic effect in 50% of the cultures inoculated. The TCID value is proportional to, but not the same as, the number of infectious virions in a sample. Titers determined using this method are typically reported as $TCID_{50}$/mL.

When no virus at all is detected by the assay, a maximum possible titer for the sample is determined using a Minimal Limit of Detection (LOD) calculation. This calculation considers the sensitivity of the assay and reports the most virus that could be in a sample without the assay detecting any. The result of these calculations is a titer reported as "≤X", meaning that the actual titer in the sample is X or lower (to a 95% certainty). This LOD calculation depends solely on the quantity of sample tested and any predilutions made to the sample before assaying. When the titer is reported as "≤X", the corresponding Log Reduction Value (LRV) is reported as "≥Y", meaning that the resulting LRV is Y or higher.

Viral clearance validation studies are designed to evaluate the ability of a MAb purification process to remove or inactivate many different kinds of viruses. The FDA recommends use of several model viruses encompassing large and small particles, DNA and RNA genomes, as well as chemically sensitive and resistant lipid enveloped and non-enveloped strains. The rationale is that demonstration of robust clearance of an appropriately diverse panel of viruses provides assurance that an undetected, unknown viral contaminant would also be reduced to minimal levels. Four viruses that fit these guidelines are shown in Table 1, which summarizes the properties of a model virus panel appropriate for MAb process viral clearance validation (adapted from ICH Q5A)

TABLE I

| Virus | Family | Natural Host | Genome Type | Envelope | Diameter (nm) | Shape | Resistance to physiochemical treatments |
|---|---|---|---|---|---|---|---|
| Minute virus of mice | Parvo | Mouse | DNA | no | 18-24 | Icosohedral | Very high |
| Xenotropic murine leukemia virus | Retro | Mouse | RNA | yes | 80-110 | Spherical | Low |
| Pseudorabies virus | Herpes | Swine | DNA | yes | 120-200 | Spherical | Medium |
| Reovirus 3 | Reo | Various | DNA | no | 60-80 | Spherical | Medium |

Generally, viral contaminants fall into two broad categories: endogenous viruses known to be present in the source material, and adventitious agents that may infiltrate the process.

The methods described herein can be used for inactivating both of these categories of viruses.

IV. Static Mixers

Although static mixers are used in other industries for in-line mixing, they have not been widely used in the pharmaceutical industry because processes generally operate in batch mode. Further, although in-line buffer mixing and dilution techniques have been described for protein purification processes (e.g. in commercial systems offered by TechniKrom, BioRad and GE Healthcare), it has not been used for virus inactivation, especially as virus inactivation is generally performed in pool tanks for large scale processes.

One skilled in the art will recognize that numerous static mixing devices can be used in the present invention, so long that the mixer disrupts the liquid flow in order to enable full mixing.

Static mixers can combine two functions in the space of one tube: flow dividing and turbulence. The flow dividing function is accomplished by a series of offset sub-elements whereby the fluid exiting one element impinges on the front blade of the next which is offset by 90 degrees. The turbulence is caused by the screw-like shape of the sub-elements which causes the fluid to rotate. Turbulence is induced by the inability of the fluid to move laminarly with the flow elements and is exaggerated by increased flow rates. The measurement of this fluidic mixing functionality is given in the Reynolds number. Re. At low flow rates and thus, low Re, the static mixers operate in the laminar flow range. This mixing function allows fresh unreacted activation fluid, such as an acidic buffer, to interact with the virus more efficiently and eliminate occlusion of the virus by old, used activation fluid. In case of a batch mixer, the process is dependent on the efficiency of sweeping away old activation fluid and replacing it with the new activation fluid.

Static mixing devices or static mixers are available in a variety of materials (e.g. stainless steel. Teflon™, copper). In selecting materials for the static mixers used in the methods described herein, it is desirable to select materials that will not react with or cause reactions in components of the sample flowing through the static mixer. It is also desirable that the material be durable and amenable to sterilization (e.g., by autoclaving or chlorine treatment), especially if the sample is to be administered to a human or other animal. A static mixer may be opaque or transparent.

In some embodiments according to the methods described herein, a static mixer is a part of a system which includes pH and mass flow control sensors at the inlet, middle and outlet of the static mixer. The relative flow rates of the sample (e.g., eluate from the upstream bind and elute chromatography step), acid and base are adjusted continuously to guarantee the desirable pH value. Control software is used that is based on the previously generated range of data so that the feedback algorithm can be model-based and therefore more efficient than traditional systems. For example, the inlet sensor cluster, pH and flow rate, can be used to determine the appropriate acid addition feed rate ($F_A$). An additional control algorithm may be used that predicts the intended final pH value at pH 2.0. If the value is not achieved correctly, the pump $F_A$ is changed to bring the fluid to the correct value. This could occur for a number of reasons, e.g., there being additional buffering capacity within the feed from the chromatographic step or the titration value may not be linear.

V. Process for Virus Inactivation Using an In-Line Static Mixer

As described above, in some embodiments according to the methods described herein, an in-line static mixer is used to achieve effective virus inactivation.

In order to enable low pH continuous virus inactivation for a continuous process, as described herein, the eluate from the previous bind and elute chromatography step in the purification process (e.g. protein A eluate) is mixed in-line with acid (usually 1 to 3 M acetic acid) using a 3-way valve and passed through a static mixer. The static mixer dimensions are chosen so as to enable efficient mixing of the acid and product streams. In order to provide sufficient residence time (typically 1-5 min) for robust virus inactivation, a tube of sufficient volume may follow after the static mixer. The virus inactivated stream is then mixed with base (usually 1-2 M tris-base at pH 11) using a 3-way valve and passed through a static mixer to enable mixing to increase the pH to a desirable pH for the next purification step in the continuous process, which is typically increased from pH 5 to 8.

The static mixer diameter and the number of elements can be chosen to enable efficient mixing depending on the total stream flow rate (i.e. feed+acid/base flow rate), density and viscosity. The flow rate is chosen to guarantee adequate residence time in conjunction with the static mixer (number and diameter) selection. The scale-up is performed by holding constant the Reynolds number. Re. Notably, in methods according to the present invention, the flow rate is maintained low enough so that Re remains in the laminar flow range.

VI. Process for Virus Inactivation Using a Surge Tank

In some embodiments according to the present invention, virus inactivation is achieved using a surge tank.

The virus inactivation methods according to the present invention may be used as part of any protein purification process, e.g., a purification process performed in a batch mode or a purification process performed in a continuous mode.

In some embodiments described herein, the virus inactivation methods are part of a continuous purification process which employs several process steps (or unit operations) that are present both upstream as well as downstream of the virus inactivation method.

In some embodiments, the bind and elute chromatography process step, which is typically performed prior to the virus inactivation step in a protein purification process, is performed in batch mode. A typical batch bind and elute chromatography operation employs a large column with multiple runs, usually 1 to 10, to process a batch of clarified cell culture feed. Accordingly, in some embodiments, once a batch process has been run, the elution pool can be collected and pumped into a surge tank to perform virus inactivation. In case of a batch bind and elute chromatography process, multiple surge tanks may be used for virus inactivation. Because of the smaller size of the surge tank, a more efficient mixing and virus inactivation is achieved.

In some other embodiments, the bind and elute chromatography process step is performed in a continuous mode. In a particular embodiment, the continuous process is a multiple continuous chromatography process, also referred to as CMC.

In case of a CMC operation, typically multiple small columns are used; with each run several (typically 10-50) cycles to process a batch of cell culture feed. Because of the small column size and a large number of cycles, a CMC approach has multiple small elutions which require virus inactivation. Instead of collecting the small elutions in a pool tank for virus inactivation, in some embodiments, a surge tank is used instead.

Use of a surge tank, as described herein, provides a better solution homogeneity more efficiently because of its smaller size and better mixing capabilities, relative to a pool tank used in conventional processes. The solution is then held for a time sufficient enough for robust virus inactivation, usually 1-30 minutes or under 1 hour, i.e. significantly shorter than what is required when using a larger pool tank. After the hold step, the pH and conductivity are adjusted in the surge tank to the desired value set for the next unit operation. The virus inactivated solution is then pumped to feed the next unit operation. Once emptied, the surge tank used for virus inactivation can be used to collect subsequent elutions, in case of the CMC process. Given appropriate timing and surge tank sizing, only one surge tank might be needed to accomplish virus inactivation in case of the CMC process. The individual elutions from the multi-column process are treated similarly for virus inactivation.

This invention is further illustrated by the following examples which should not be construed as limiting. The contents of all references, patents and published patent applications cited throughout this application, as well as the Figures, are incorporated herein by reference.

EXAMPLES

Example 1. Time Dependence of X-MuLV Low-pH Virus Inactivation in Test Tubes

In this representative experiment, a retrovirus spiked into a solution containing a MAb is inactivated by short-time incubation at low pH. The goal of the experiment is to understand the pH and exposure time required for complete retrovirus inactivation in a solution containing high concentrations of protein (antibody). The minimal time required to inactivate X-MuLV is determined at pH's ranging from 3.1-3.5. The experiment is performed in test tubes. The maximum experimental time tested for inactivation is five minutes using a static mixer.

The sample used is 20 mg/ml, polyclonal IgG (Seracare) in 50 mM sodium acetate buffer at pH 5.3. The predilution used to avoid cytotoxicity from the buffer is 1/50. In order to meet the target of LRV >4. X-MuLV stock of titer 7.0 TCID50/mL is used to spike feed to 6.0 log TCID50/mL (~10% spike). Accounting for the 1/50 predilution and the ~1/5 dilution of the material in the process of acidifying and neutralizing the sample (1/250 altogether), this results in an observed LRV of >4.44 (assuming target spike level is achieved). Assay media used is standard X-MuLV titration media: McCoys+1% FBS, 1× penicillin/streptomycin, 1×L-glutamine, 1×NEAA. The results are summarized in Table II below.

TABLE II

| X-MuLV log reduction values (LRV) | | | |
|---|---|---|---|
| target pH | ~7 | 3.10 | 3.50 |
| actual pH | ~7 | 2.85 | 3.36 |
| 1 min | not tested | ≥4.36 | ≥4.75 |
| 3 min | not tested | ≥4.36 | ≥4.75 |
| 5 min | 0.1 | ≥4.36 | ≥4.75 |

The results clearly indicate that X-MuLV is rapidly inactivated to the point of non-detection within one minute at both pH 2.85 and 3.36. No inactivation is seen at pH 7. The high protein concentration (20 mg/mL Seracare polyclonal IgG) of these buffers is not an impediment to achieving rapid inactivation (See, e.g. Kurt Brorson et al. "Bracketed Generic Inactivation of Rodent Retroviruses by Low pH Treatment for Monoclonal Antibodies and Recombinant Proteins," Biotech.Bioeng. Vol. 82. No. 3 (2003))

Example 2. Time Dependence of X-MuLV Low-pH Virus Inactivation in Test Tubes for Both polyclonal and Monoclonal Antibodies In this representative experiment, the same protocol as described in Example 1 is followed, in order to better understand at what pH there is no virus inactivation, or alternatively, the minimum pH1 where there is inactivation.

Both polyclonal IgG (Seracare) and two monoclonal antibodies (MAb05 and MAb04) produced in CHO cells are used. The results are summarized in Table III below, where the results with "≥" indicate that no virus is detected in the sample.

TABLE III

| MAb5 | | MAb04 | | Seracare | | Seracare | |
|---|---|---|---|---|---|---|---|
| time (min) | LRV @ pH 3.7 | time (min) | LRV @ pH 3.7 | time (min) | LRV @ pH 4 | time (min) | LRV @ pH 5 |
| 1.3 | 3.27 | 1.4 | 2.51 | 10 | 0.51 | 10 | 0 |
| 2.3 | 3.45 | 2.3 | 2.9 | 20 | 1.01 | 20 | 0 |
| 5 | 3.54 | 5 | 3.1 | 30 | 1.01 | 30 | 0 |
| 10 | ≥4.3 | 10 | ≥4.0 | 45 | 1.01 | 45 | 0.13 |
| | | | | 60 | 1.26 | 60 | 0 |

As results in Table III indicate that half a minute is adequate for virus inactivation at pH 3.3. Increasing the pH to 3.6 extends the time needed to 1.1 minutes. Ten minutes are required at pH above pH 3.6, while at pH 4 and above, no virus inactivation is observed even with one hour exposure.

Example 3. Time Dependence of X-MuLV Low-pH Virus Inactivation with Static Mixers In this representative experiment, the pH and exposure time required for complete retrovirus inactivation in a high protein (MAb) feed solution using static mixers is investigated.

Based on the results in Example 1, the possibility of inactivating a retrovirus using in-line static mixers is investigated. The pH of the solution is lowered as it flows through a channel by injection of acid at a rate calculated for reducing the pH to 3.4. At the downstream end of the channel, the pH is adjusted back to neutral for the next step in the process. This experiment determines the exposure time needed to inactivate X-MuLV using an in-line technique. The experimental setup is shown in FIG. 1.

The sample used is 9.9 g/L polyclonal IgG (Seracare) in 20 mM acetic acid buffer at pH 5.0. The feed spiked with virus is passed through the experimental set-up shown in FIG. 1 for in-line pH inactivation. The set-up consists of: (a) a peristaltic pump to transfer the sample feed; (b) two syringe pumps to deliver acid and base; (c) two in-line pH probes; and (d) two static mixers. The flow rates are predetermined in batch mode based on the amount of acid/base needed to achieve the pH of interest. The residence time for virus inactivation is altered by having tubes of appropriate diameter and length used after static mixer and before the pH probe. The results are summarized in Table IV below.

TABLE IV

| Seracare | | Seracare | |
|---|---|---|---|
| time (min) | LRV @ pH 3.3 | time (min) | LRV @ pH 3.6 |
| 0.5 | ≥3.6 | 0.6 | 2.80 |
| 0.9 | ≥3.6 | 1.1 | ≥3.6 |
| 1.4 | ≥3.6 | 1.7 | ≥3.6 |
| 2.3[#] | ≥3.6 | 2.8[#] | ≥3.6 |
| 3.5 | ≥3.6 | 4.4 | ≥3.6 |

[#]3 fractions, in succession, for 90 seconds each are collected to ensure consistent virus inactivation in the 4.5 min time frame As summarized in Table IV, complete inactivation is observed at pH 3.3 for all the time points. For pH 3.6, time≥1.1 min gives complete inactivation. In addition, the fractions collected at residence times 2.3 and 2.8 min show complete virus inactivation over the 4.5 min time frame of data collection, thereby indicating that in-line low pH virus inactivation is consistent over time.

Example 4. Time Dependence of X-MuLV Low-pH Virus Inactivation with Static Mixers In this representative experiment, the pH and exposure time required for complete retrovirus inactivation in a high protein (MAb) feed solution when using static mixers is investigated. The experimental setup is shown in FIG. 1.

The sample used is 20 mg/mL polyclonal IgG (Seracare) in 50 mM sodium acetate buffer at pH 5.3. The predilution used to avoid cytotoxicity from the buffer is 1/50. In order to meet the target of LRV >4, X-MuLV stock of titer 6.9 TCID50/mL is used to spike feed to 5.6 log TCID50/mL (~10% spike). Assay media used is standard X-MuLV titration media: McCoys+1% FBS, 1× penicillin/streptomycin, 1×L-glutamine, 1×NEAA.

For the acidification and neutralization, 3 M acetic acid and 2 M tris buffer are used. Control samples are also generated using only tubes (no static mixer) in order to directly check the effect of the static mixer. The results are summarized in Table V below.

TABLE V

| Sample | Time (min) | Titer (log TCID50) | LRV |
|---|---|---|---|
| pH 7 Hold | >60 | 3.8 | n/a |
| pH 3.4 with static mixer | 0.5 | ≤1.5 | ≥2.2, <4.3 |
| | 1 | 2.9 | 0.9 |
| | 2 | ≤−0.5 | ≥4.3 |
| | 3 | ≤−0.5 | ≥4.3 |
| pH 3.4 without static mixer | 0.25 | 3.3 | 0.4 |
| | 0.5 | 3.3 | 0.5 |
| | 1 | 3.1 | 0.7 |
| | 2 | 3.0 | 0.7 |

TABLE V-continued

| Sample | Time (min) | Titer (log TCID50) | LRV |
|---|---|---|---|
| pH 7 with static mixer | 3 | 4.1 | −0.3 |
| TFF/UC 2.4 Prep (positive control) | n/a | 6.5 | n/a |

As summarized in Table V, no virus inactivation is observed for the positive control and the two samples exposed to pH 7, either when held in a test tube or when passed through a static mixer at the maximum exposure time, 3 min. The samples taken through the static mixer show complete virus inactivation at times longer than one minute. Static mixer is critical for virus inactivation as very little inactivation occurs in its absence. At least two minutes at target pH 3.4 is required to achieve >4 LRV of X-MuLV. The static mixer itself does not cause any inactivation at neutral pH.

Example 5. Time Dependence of X-MuLV Virus Inactivation Using Caprylic Acid and Detergents in Test Tubes In this experiment, virus inactivation is performed in a test tube in order to determine the minimum time and pH requirements for virus inactivation when using various additives, such as caprylic acid and detergents such as Triton X, Tween and combinations thereof.

Both pure Mab in buffer as well as Mab in clarified cell culture are used in this experiment. While the foregoing additives are known to effect virus inactivation, this example demonstrates that by using static mixers, virus inactivation can be obtained in shorter time frame. The results of this representative experiment are shown in Table VI.

TABLE VI

| | Pure MAb07 | | | | | MAb05 cell culture | | |
|---|---|---|---|---|---|---|---|---|
| Time (min) | Caprylate 200 mM pH 7 | Caprylate 20 mM pH 5.5 | Triton X (0.5%) | Tween (1%) | TNBP/ Tween 20 | Caprylate 200 mM pH 7 | Caprylate 20 mM pH 5.5 | Triton X (0.5%) |
| 0 | 0 | 0 | 0 | 0 | 0 | 0 | 0 | 0 |
| 1 | ≥3.1 | ≥3.1 | ≥3.1 | 0.5 | ≥3.1 | 2.91 | 2.63 | ≥3.1 |
| 5 | ≥3.1 | ≥3.1 | ≥3.1 | 1 | ≥3.1 | ≥3.8 | ≥3.8 | ≥3.1 |
| 10 | ≥3.1 | ≥3.1 | ≥3.1 | 1.8 | ≥3.1 | ≥3.8 | ≥3.8 | ≥3.1 |
| 20 | ≥3.1 | ≥3.1 | ≥3.1 | 2.2 | ≥3.1 | ≥3.8 | ≥3.8 | ≥3.1 |

As shown in Table VI, in the case of purified MAb, one minute appears to be adequate for complete virus inactivation with all additives used except for Tween. In case of the clarified cell culture, only Triton X at 0.5% results in complete virus inactivation after one minute, while caprylate at both pH and salinities requires a minimum of five minutes.

Example 6. Effect of Salt and MAb Concentration on X-MuLV Virus Inactivation at pH 3.6 Using Static Mixers In this representative experiment, the effect of MAb and salt concentration on the minimum time and pH require for virus inactivation is investigated. MAb is prepared to 21.8 g/L using 20 mM acetic acid, pH 3.2 and then titrated to pH 5.0 using 10 M NaOH. The conductivity of that solution is 1.4 mS/cm. The lower concentrations are made by diluting with 20 mM acetic acid, pH 3.2 and then titrated to pH 5 using 10 M NaOH. The conductivity of these solutions is 1.4 mS/cm. The high salt solution is adjusted by NaCl addition to a final molarity of 250 mM. All solutions are adjusted to pH 3.6 for virus inactivation using the inline static mixer setup. The results are summarized in Table VII.

TABLE VII

| [IgG] g/L | [NaCl] mM | time (sec) | LRV |
|---|---|---|---|
| 4.4 | 0 | 20 | 2.8 |
| 4.4 | 0 | 40 | 3.5 |
| 4.4 | 0 | 60 | 3.5 |
| 4.4 | 250 | 20 | 3.9 |
| 4.4 | 250 | 40 | 4 |
| 4.4 | 250 | 60 | 4 |
| 21.8 | 0 | 20 | 3.5 |
| 21.8 | 0 | 40 | ≥4.3 |
| 21.8 | 0 | 60 | ≥4.3 |

As summarized in Table VII, the most relevant solution is the one with a high concentration of MAb and the low salt concentration, which mimics a Protein A elution pool. For such a sample, 40 seconds are found to be sufficient for complete virus inactivation at a pH of 3.6.

Example 7. Effect of pH on X-MuLV Virus Inactivation Using Static Mixers

In this representative experiment, the effect of pH on virus inactivation using static mixers is investigated. IgG is prepared to 9 g/L using 20 mM acetic acid, pH 3.2 and then titrated to pH 5.0 using 10 M NaOH. All solutions are then adjusted to the desired pH for virus inactivation using the in-line static mixer setup. The results are summarized in Table VIII below.

TABLE VIII

| time (sec) | LRV @ pH 3.4 | LRV @ pH 3.5 | LRV @ pH 3.6 |
|---|---|---|---|
| 20 | 3.2 | 3.1 | 3.1 |
| 40 | ≥4 | ≥4 | 3.2 |
| 60 | ≥4 | ≥4 | ≥4 |

As shown in Table VII, about one minute is required for complete virus inactivation at pH 3.6, whereas even shorter times are adequate at lower pH.

Example 8. Effect of Temperature on X-MuLV Virus Inactivation Using Low pH

In this representative experiment, the effect of temperature on virus inactivation is investigated. Generally, in-line virus inactivation is particularly conducive to exposure of the solution to higher temperatures; therefore, it is important to determine the effect of temperature on virus inactivation.

The feed used in this study is 9.9 g/L. Seracare polyclonal IgG in 20 mM sodium acetate, pH 5.0. Three aliquots of 25 mL each are transferred into three separate 50 mL centrifuge tubes. To 25 mL of this feed, 1.4 mL of 3 M acetic acid, pH 2.5 is added to bring down the pH to pH 3.7. One of the centrifuge tubes is left at room temp at 22 C. The other two centrifuge tubes are then placed in water baths set at 10° C., and 35° C. Upon equilibration, the temperature and pH of the liquid in the tubes is measured (see, Table IX below). A 10% virus spike is subsequently added to each of the tubes. 5 mL samples are collected at the stipulated time points and 0.4 mL of 2 m tris-base, pH 11.0 is added to increase the pH to pH 7.0.

TABLE IX

| Time (min) | pH 3.6 @ 12° C. | pH 3.67 @ 22° C. | pH 3.78 @ 33° C. |
|---|---|---|---|
| 1 | 3.3 | ≥4.1 | ≥4.0 |
| 2 | ≥4.3 | ≥4.1 | ≥4.0 |
| 5 | ≥4.3 | ≥4.1 | ≥4.0 |
| 10 | ≥4.3 | ≥4.1 | ≥4.0 |

The results summarized in Table IX indicate that high temperature is preferred for virus inactivation. It is surprising that even with a higher measured pH, the higher temperature achieves complete inactivation at the 1 minute time point.

Example 9. Use of Static Mixers to Accelerate pH Stabilization

In this representative experiment, the use of static mixers to accelerate pH stabilization was investigated. In general, it is desirable that the time needed for the pH to reach its desired value is minimized.

In this example, experiments are done at various flow rates and tube lengths and diameters, all selected so that only laminar flow is achieved, i.e. with Reynolds number below 100. The starting and target desired pH values are 5.0±0.1 and 3.3±0.1, respectively.

The time needed to reach the desired target pH value is recorded as a function of time or solution volume processed. The volume is expressed in terms of tube dead volumes and data is collected at a flow rate of 10 mL/min. The results are summarized in Table X below.

TABLE X

| | Reynolds # | # of dead volumes (dimensionless units) |
|---|---|---|
| No static mixer | 40-50 | 5 |
| 12 static mixer elements | 10-100 | 3 |
| 24 static mixer elements | <10 | 2 |

The results shown in Table X indicate that pH stabilization occurs faster when using more static mixer elements, while still remaining well into the laminar flow.

Example 10. In-Line Virus Inactivation on Protein A Eluate

In this representative experiment, a clarified cell culture of a MAb is subjected to Protein A chromatography. The Protein A eluate is collected in ten separate fractions, spanning about three column volumes. Each fraction is separately adjusted to two pH values, 3.3 and 3.6. The amounts of acid needed to reduce the pH to the desired value and of base needed to then increase the pH1 to the desired value are determined, as described herein. These amounts are different for each fraction because the different amounts of MAb result in different buffering capacity for each sample.

A model is then built of the amounts of acid and base as a function of eluate volume. A second experiment is performed where the Protein A eluate is continuously adjusted to the desired pH based on the model built. Virus concentration is measured following virus inactivation to confirm that virus inactivation is achieved.

Example 11. Effect of In-Line Virus Inactivation on MAb Quality

In this representative experiment, the beneficial effect of shorter exposure time on MAb product quality is investigated. Two monoclonal antibodies are purified using Protein A chromatography, samples are collected in test tubes and immediately incubated at various pH (i.e., pH 3, 3.3, 3.6 and 4) and times (i.e. 1, 2, 5 and 15 and 90 minutes).

The samples are then neutralized and tested for presence of aggregates by Size Exclusion Chromatography (SEC) and SDS gels and for changes in charge variants by weak cation exchange chromatography (WCX-10). The identity of the resulting protein is also analyzed by Liquid Chromatography/Mass Spectrometry (LC/MS).

The specification is most thoroughly understood in light of the teachings of the references cited within the specification which are hereby incorporated by reference. The embodiments within the specification provide an illustration of embodiments in this invention and should not be construed to limit its scope. The skilled artisan readily recognizes that many other embodiments are encompassed by this invention. All publications and inventions are incorporated by reference in their entirety. To the extent that the material incorporated by reference contradicts or is inconsistent with the present specification, the present specification will supercede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

What is claimed is:

1. A method of inactivating one or more viruses in a Protein A eluate as the Protein A eluate flows from a Protein A affinity chromatography step to a flow-through purification step, the method comprising mixing the Protein A eluate with one or more virus inactivating agents using one or more in-line static mixers, wherein the flow of the Protein A eluate through the static mixer is in the laminar flow range comprising a Reynolds number below 100, wherein complete virus inactivation is achieved in less than 10 minutes or less than 5 minutes or less than 2 minutes or less than 1 minute.

2. A method for inactivating one or more viruses, the method comprising:
   a. subjecting a sample comprising a target protein to a Protein A affinity chromatography process, thereby to obtain an eluate; and
   b. continuously transferring the eluate to an in-line static mixer to mix one or more virus inactivating agents with the eluate for a duration of time which is equal to or less than 10 minutes, wherein the flow of the eluate through the static mixer is in the laminar flow range comprising a Reynolds number below 100, thereby to inactivate one or more viruses.

3. The method of claim 2, wherein the Protein A affinity chromatography process is performed in batch mode.

4. The method of claim 2, wherein the Protein A affinity chromatography process is performed in a continuous mode.

5. The method of claim 4, wherein the process comprises continuous multi-column chromatography.

6. The method of claim 2, wherein the one or more virus inactivating agents is an acid.

7. The method of claim 2, wherein the target protein is an antibody.

8. The method of claim 2, further comprising the step of continuously transferring output from step (b) into a flow-through purification process step.

9. The method of claim 8, wherein the flow-through purification step comprises two or more matrices selected from activated carbon, anion exchange media, cation exchange media and virus filter.

10. The method of claim 1, wherein the flow-through purification step comprises two or more matrices selected from activated carbon, anion exchange media, cation exchange media and virus filter.

* * * * *